(12) United States Patent
Gale et al.

(10) Patent No.: US 9,345,816 B2
(45) Date of Patent: May 24, 2016

(54) METHODS OF TREATMENT WITH DRUG DELIVERY AFTER BIODEGRADATION OF THE STENT SCAFFOLDING

(71) Applicant: Abbott Cardiovascular Systems Inc., Santa Clara, CA (US)

(72) Inventors: David C. Gale, Kennesaw, GA (US); Bin Huang, Pleasanton, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 26 days.

(21) Appl. No.: 14/531,744

(22) Filed: Nov. 3, 2014

(65) Prior Publication Data
US 2015/0057745 A1    Feb. 26, 2015

Related U.S. Application Data

(60) Continuation of application No. 13/925,750, filed on Jun. 24, 2013, now Pat. No. 8,876,890, which is a continuation of application No. 13/185,370, filed on Jul. 18, 2011, now Pat. No. 8,469,968, which is a division of application No. 11/823,703, filed on Jun. 27, 2007, now Pat. No. 8,016,879, which is a continuation-in-part of application No. 11/582,706, filed on Oct. 17, 2006, now abandoned.

(60) Provisional application No. 60/834,885, filed on Aug. 1, 2006.

(51) Int. Cl.
*A61L 31/14* (2006.01)
*A61F 11/00* (2006.01)
*A61L 31/16* (2006.01)
*A61F 2/82* (2013.01)

(52) U.S. Cl.
CPC . *A61L 31/14* (2013.01); *A61F 2/82* (2013.01); *A61L 31/146* (2013.01); *A61L 31/148* (2013.01); *A61L 31/16* (2013.01); *A61L 2300/41* (2013.01); *A61L 2300/416* (2013.01); *A61L 2300/604* (2013.01)

(58) Field of Classification Search
CPC ............... A61F 2/04; A61F 2/06; A61F 2/91; A61F 2/82; A61L 31/16; A61L 31/14; A61L 31/146
See application file for complete search history.

(56) References Cited

U.S. PATENT DOCUMENTS

| 6,423,092 B2 * | 7/2002 | Datta ........................ A61F 2/88 623/1.15 |
| 2005/0033412 A1 * | 2/2005 | Wu ........................ A61F 2/0077 623/1.15 |

* cited by examiner

*Primary Examiner* — Jason-Dennis Stewart
(74) *Attorney, Agent, or Firm* — Squire Patton Boggs (US) LLP

(57) ABSTRACT

Disclosed is a stent comprising a bioabsorbable polymeric scaffolding; and a plurality of depots in at least a portion of the scaffolding, wherein the plurality of depots comprise a bioabsorbable material, wherein the degradation rate of all or substantially all of the bioabsorbable polymer of the scaffolding is faster than the degradation rate of all or substantially all of the bioabsorbable material of the depots.

8 Claims, 3 Drawing Sheets

METHODS OF TREATMENT WITH DRUG DELIVERY AFTER BIODEGRADATION OF THE STENT SCAFFOLDING

CROSS REFERENCE TO RELATED APPLICATION

This application is a continuation of U.S. application Ser. No. 13/925,750 filed Jun. 24, 2013 which is a continuation of U.S. application Ser. No. 13/185,370 filed Jul. 18, 2011 which is a division of U.S. application Ser. No. 11/823,703, filed on Jun. 27, 2007 and published on Feb. 28, 2008 as U.S. Patent Application Publication No. 2008-0051880 A1, and issued on Sep. 13, 2011, as U.S. Pat. No. 8,016,879, which claims the benefit of U.S. Provisional Patent Application No. 60/834,885, filed on Aug. 1, 2006, and U.S. application Ser. No. 11/823,703 is also a continuation in part of U.S. application Ser. No. 11/582,706, filed on Oct. 17, 2006 and published on Apr. 17, 2008 as U.S. Patent Application Publication No. 2008-0091262 A1. All of these applications are incorporated by reference herein in their entirety, including any drawings.

BACKGROUND OF THE INVENTION

1. Field of the Invention

This invention generally relates to a stent for treating a disorder with a drug over a period of time extending beyond biodegradation of the stent scaffolding.

2. Description of the Background

In particular, the invention relates to radially expandable endoprostheses that are adapted to be implanted in a body lumen. An "endoprosthesis" corresponds to an artificial device that is placed inside the body. A "lumen" refers to a cavity of a tubular organ such as a body lumen. A stent is an example of such an endoprosthesis. Stents are generally cylindrically shaped devices which function to hold open and sometimes expand a segment of a body lumen or other anatomical lumen such as urinary tracts and bile ducts. Stents are often used in the treatment of atherosclerotic stenosis in body lumens. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a body lumen or heart valve after it has been subjected to angioplasty or valvuloplasty.

The treatment of a diseased site or lesion with a stent involves both delivery and deployment of the stent. "Delivery" refers to introducing and transporting the stent through a body lumen to the treatment area in a body lumen. "Deployment" corresponds to the expanding of the stent within the lumen at the treatment area. Delivery and deployment of a stent are accomplished by positioning the stent at one end of a catheter, inserting the end of the catheter through the skin into a body lumen, advancing the catheter in the body lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock.

When the stent is in a desired bodily location, the sheath may be withdrawn allowing the stent to self-expand. This requires a sufficient degree of strength and rigidity or stiffness. In addition to having adequate radial strength, the stent should be longitudinally flexible to allow it to be maneuvered through a tortuous vascular path.

Thus, a stent is typically composed of a scaffolding that includes a pattern or network of interconnecting structural elements or struts. The scaffolding can be formed of tubes, or sheets of material rolled into a cylindrical shape. The scaffolding is designed to allow the stent to be radially expandable. The pattern is generally designed to maintain the longitudinal flexibility and radial rigidity required of the stent. Longitudinal flexibility facilitates delivery of the stent and radial rigidity is needed to hold open a body lumen. A medicated stent may be fabricated by coating the surface of either a metallic or polymeric scaffolding with a polymeric carrier that includes a bioactive agent. The polymeric scaffolding may also serve as a carrier of bioactive agent.

In many treatment applications of stents, the presence of a stent in a body may be necessary for a limited period of time until its intended function of, for example, maintaining vascular patency and/or drug delivery is accomplished. Thus, stents are often fabricated from biodegradable, bioabsorbable, and/or bioerodable materials such that they completely erode only after the clinical need for them has ended. In addition, a stent should also be capable of satisfying the mechanical requirements discussed above during the desired treatment time.

A polymeric stent should be mechanically stable throughout the range of stress experienced during use. In addition to mechanical stability, a stent should have a sufficient rate of biodegradability or erosion as dictated by a treatment regimen. However, one of the major clinical challenges of bioabsorbable stents is adequately suppressing inflammatory responses triggered by the degradation of the stent. The embodiments of the invention address this and other concerns.

SUMMARY OF THE INVENTION

Disclosed is a stent comprising a bioabsorbable polymeric scaffolding; and a plurality of depots in at least a portion of the scaffolding, wherein the plurality of depots comprise a bioabsorbable material, wherein the degradation rate of all or substantially all of the bioabsorbable polymer of the scaffolding is faster than the degradation rate of all or substantially all of the bioabsorbable material of the depots.

Also disclosed is a method treating a body lumen, the method comprising providing a stent comprising a scaffolding having a plurality of depots, wherein the scaffolding degrades at a faster rate than a material in the plurality of depots and deploying the stent at a treatment area in a body lumen.

Also disclosed is a method of treating a body lumen, the method comprising deploying a first stent at a treatment area, wherein the first stent includes a bioabsorbable polymeric scaffolding and a plurality of depots in at least a portion of the scaffolding, wherein the depots have a bioabsorbable material, and wherein the degradation rate of all or substantially all of the bioabsorbable polymer of the scaffolding is faster than the degradation rate of all or substantially all of the bioabsorbable material in the depots and deploying a second stent in at least a portion of the treatment area.

DETAILED DESCRIPTION

Figure 1:
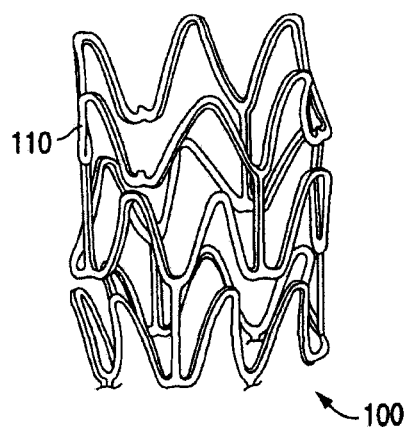
FIG. 1 depicts a stent.

A common disorder associated with mechanical modification of a vessel, such as by a balloon or stenting is restenosis. A number of cellular mechanisms have been proposed that lead to restenosis of a vessel, such as inflammatory response to injury and foreign body presence.

Inflammation is a defensive, biological response to injury, infection, or an abrupt change in tissue homeostasis. In nature, inflammatory responses are designed to destroy, dilute and isolate injurious agents and then lead to recovery and repair of the affected tissue. Vascular inflammation is the first stage of the inflammatory response, developing after the initial contact with the stimulus and continuing sometimes for several days. The presence of a stimulatory agent in the blood or in the tissue triggers the body's response through endothelial cells. The endothelial cell layer is the innermost layer of larger vessels and the only cell layer of the smallest vessels, the capillaries.

Additionally, the presence of a biodegradable foreign body, such as a biodegradable stent in a vessel can lead to or aggravate an inflammatory response, thus leading to more aggressive restenosis.

Biodegradation refers generally to changes in physical and chemical properties that occur (e.g., in a polymer) upon exposure to bodily fluids as in a vascular environment. The changes in properties may include a decrease in molecular weight, deterioration of mechanical properties, and decrease in mass due to erosion or absorption. The decrease in molecular weight may be caused by chemical reactions of bodily fluids with the polymer, for example, hydrolysis and/or metabolic processes. By-products of such degradation reactions can be responsible for inciting inflammation. For example, by-products of hydrolysis are produced when polymer molecules are cleaved into component parts by the addition of water. Various by-products of degradation of biodegradable polymers are known to incite an inflammatory response. For example, lactic acid, a degradation by-product of poly(lactic acid) polymers, is known to cause an inflammatory response.

Furthermore, the release of by-products into the body from a biodegradable stent occurs continuously from the time of first exposure to bodily fluids to a time when the stent is either completely degraded and eliminated or removed from the body. It follows that throughout this time frame, the body is continuously exposed to inflammation-inciting by-products. Therefore, it is desirable for the stent to degrade rapidly once the need for support of the lumen has expired.

Described herein is a drug-delivery stent that allows delivery of drug even after the stent scaffolding has degraded. Thus, the stent scaffolding need not remain in the body lumen to deliver drug. The stent scaffolding may be made to degrade rapidly and completely or substantially completely disappear once the need for support of the lumen has expired. The drug-delivery stent described herein includes one or more drugs for treating a vascular disorder or a related disorder. The drugs, for example, can be a combination of at least one anti-proliferative agent, at least one anti-inflammatory agent, and optionally other types of bioactive agents.

Embodiments also disclose a method of delivering a drug into a lumen. The method provides for implanting a medical device, such as a stent, that may include depots at a surface of the stent containing a depot material which degrades at a slower rate than a stent scaffolding. Alternatively, or in addition to the depots, the stent may include a coating material above a surface of the stent which degrades at a slower rate than the scaffolding. The coating and/or depot material is used for carrying a variety of drugs including but not limited to therapeutic substances and polymers impregnated with therapeutic substances. The drug from the coating and/or depot material can be released into the lumen after the scaffolding of the stent has degraded.

Certain embodiments provide for a rapidly degrading scaffolding that degrades within 6 months, within 3 months, or more narrowly within 2 months. Re-stenting is facilitated by rapid degradation of the first stent's scaffolding, enabling a second stent to be implanted in the stented area or treatment area within only a few months after the first stent has been implanted. When the second stent is deployed in the treatment area, the functional lumen diameter is not reduced as is the case when a second stent is deployed at a treatment area of a first stent that has only partially degraded or not degraded at all in the case of a stent made from a non-degradable material. In the latter case, the reduced functional diameter causes the blood flow to fall significantly and possibly congest the lumen.

As discussed above, a drug(s) may be included in a coating and/or depot material, of the first stent. Thus, when the second stent is implanted, the first stent may deliver drug from at least a portion of the coating and/or depot material of the first stent while the second stent is implanted. For example, an anti-inflammatory agent may be included within the coating and/or depot material of the first stent, such that when the second stent is implanted, the anti-inflammatory agent continues to deliver drug to prevent inflammation. In addition, the anti-inflammatory agent that is delivered from the coating and/or depot material of the first stent may also effectively suppress inflammation of a lumen during all or a majority of the degradation of the scaffolding of the first stent.

In a further embodiment, a drug is included in the coating, in a plurality of depots, and/or the scaffolding of the stent, and is designed to have release parameters for drugs included. The second stent may or may not include a coating, a plurality of depots, or a drug. The second stent may have a biostable or biodegradable scaffolding made from a metal, polymer, or combination thereof. The drug mixed or dispersed within a biodegradable scaffolding may be delivered into a lumen at substantially the same, a faster rate, or a slower rate as the scaffolding degrades. In one embodiment, the drug may be incorporated within the scaffolding during fabrication of the stent according to those of skill in the art. For example, an anti-inflammatory agent may be incorporated in the scaffolding, and configured to be delivered through the coating and/or depot material in a plurality of depots to treat inflamed portions of lumen.

Moreover, the properties of the coating and/or depot material, such as thickness and porosity, may influence the rate of release of the drug(s) from the stent. Some embodiments may include controlling the release rate of the drug by modifying the properties of the coating and/or depot material.

A biodegradable stent can remain in the body and a drug can be delivered in the body for a duration of time at least until its intended function of, for example, maintaining vascular patency and drug delivery is accomplished. Biodegradable polymers are used to form the stent, such that the entire stent can be made to disappear after the process of degradation, erosion, or absorption. In some embodiments, very negligible traces of polymer or residue are left behind. The duration is typically in the range of 6-12, 6-18, or 6-24 months, for example. The time needed to maintain vascular patency can be shorter than the drug delivery time.

The term "stent" is intended to include, but is not limited to, self-expandable stents, balloon-expandable stents, stent-grafts, and grafts. The structure of the stent can be of virtually any design. A stent, for example, may include a pattern or network of interconnecting structural elements or struts. FIG. 1 depicts an example of a three-dimensional view of a stent 100. The stent may have any pattern that includes a number of interconnecting elements or struts 110. As depicted in FIG. 1 the geometry or shape of stents vary throughout its structure. In some embodiments, a stent may be formed from a tube by laser cutting the pattern of struts into the tube. The stent may also be formed by laser cutting a polymeric sheet, rolling the pattern into the shape of the cylindrical stent, and providing a longitudinal weld to form the stent.

Figure 2A:
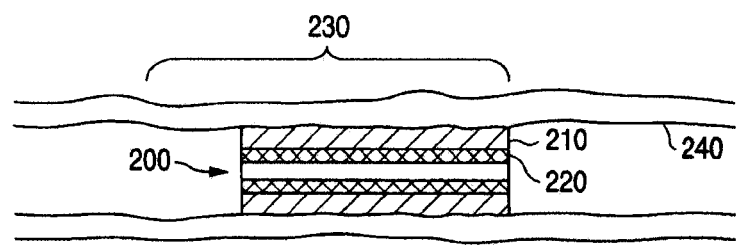
FIG. 2(a) depicts a cross-section of a stent implanted in a body lumen, the stent having a scaffolding and a drug coating.
Figure 2B:
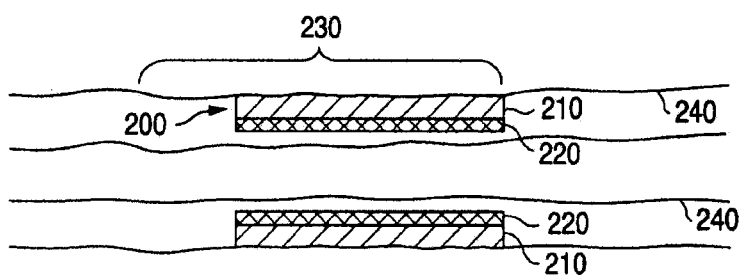
FIG. 2(b) depicts the stent of FIG. 2(a) after endothelialization of the stent in the body lumen.

FIG. 2(a) depicts a cross section of a stent implanted in a body lumen. A stent 200 according to one embodiment of the invention includes a bioabsorbable polymeric scaffolding 210 and a coating material 220 on at least a portion of the scaffolding 210. Coating material 220 may include a drug and a bioabsorbable polymer. Although coating material 220 is only depicted in FIGS. 2(a) and 2(b) as being on one of stent 200, it should be understood by those skilled in the art that stent 200 can also be coated on the other side of stent 200. In one embodiment, the degradation rate of all or substantially all of scaffolding 210 is faster than the degradation rate of all or substantially all of coating material 220. Thus, the defined degradation time of all or substantially all of scaffolding 210 is shorter than the degradation time of all or substantially all coating material 220. By providing a scaffolding 210 that has a faster degradation rate than its coating 220, scaffolding 210 degrades away or disappears, while coating material 220 continues to deliver drug. In one embodiment, coating material 220 continues to deliver drug after scaffolding 210 has completely degraded. FIG. 2(b) depicts stent 200 after endothelialization of stent 200 in lumen wall 240. In one embodiment, all or substantially all of coating material 220 degrades faster than all or substantially all of scaffolding 210. In another embodiment, coating material 220 continues to elute drugs even after scaffolding 210 no longer supports lumen wall 240.

Figure 2C:
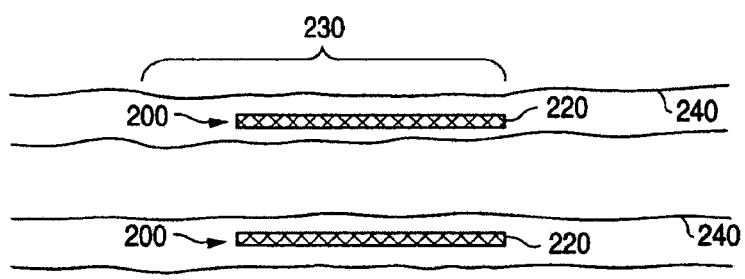
FIG. 2(c) depicts the stent of FIG. 2(a) after endothelialization of the stent and degradation of the scaffolding, where the drug coating of the stent remains lodged in the lumen and continues to deliver drug in the lumen.

Turning now to FIG. 2(c), with continual reference to FIG. 2(b), coating material 220 remains lodged in lumen wall 240 after scaffolding 210 substantially degrades. Because coating material 220 can be made to deliver drug even after the disintegration of scaffolding 210, the invention enables stent 200 to release drug for an extended period of time throughout the life of stent 200 while scaffolding 210 degrades, and if desired, long after scaffolding 210 degrades. In one embodiment, stent 200 delivers drug for over 50% of the life of scaffolding 210. In another embodiment, stent 200 delivers drug for over 80% of the life of scaffolding 210. In yet another embodiment, stent 200 delivers drug for the entire life of scaffolding 210, or 100% of the life of scaffolding 210. Thus, after the entire scaffolding 210 has completely degraded, coating material 220 may be designed to continue to deliver drug, as depicted in FIG. 2(c).

Figure 3:
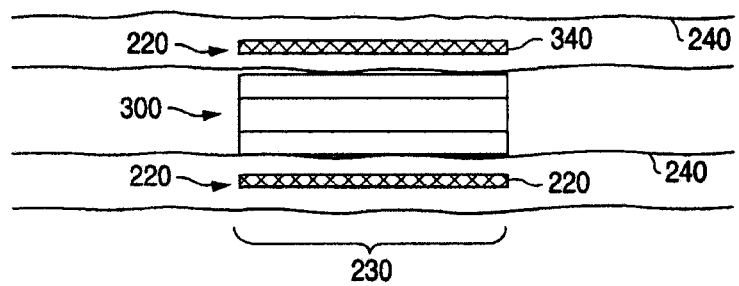
FIG. 3 depicts a second stent that is implanted at a treatment area of a first stent, where the scaffolding (not depicted) of the first stent has degraded but the coating of the first stent remains lodged in the lumen wall.

In one embodiment, upon deployment of stent 200 in a treatment area, scaffolding 210 substantially or completely degrades from the treatment area before coating 220 substantially or completely degrades. In another embodiment, coating 220 delivers a drug to lumen wall 240 during degradation of scaffolding 210 and after substantial or complete degradation of scaffolding 210. In yet another embodiment, coating 220 becomes endothelialized in a lumen wall 240 and delivers a drug after scaffolding 210 has substantially or completely degraded. Depicted in FIG. 3 is a second stent 300 that has been implanted in the same treatment area 230 as the first stent, where the scaffolding (not depicted) of the first stent has degraded but coating material 220 of first stent remains lodged in the lumen wall. In some embodiments, second stent 300 is implanted in lumen wall 240 after endothelialization of first stent. In some embodiments, second stent 300 is implanted in lumen wall 240 after a scaffolding (not depicted) of a first stent is at least partially degraded, substantially degraded, or more narrowly, completely degraded in lumen wall 240. In some embodiments, second stent 300 is deployed in treatment area 230 when scaffolding (not depicted) of the first stent is greater than 50% degraded, greater than 75% degraded, and more narrowly, greater than 95% degraded.

In one embodiment, second stent 300 may be implanted in treatment area 230 after all or substantially all of scaffolding (not depicted) of first stent has degraded, such that only a coating material 220 of the first stent remains in lumen wall 240. In certain embodiments, coating material 220 of the first stent continues to deliver drug in lumen wall 240 when second stent 300 is implanted.

As mentioned above, second stent 300 is deployed when the scaffolding (not shown) of the first stent has at least partially degraded, has substantially degraded, or has completely degraded. Thus, embodiments disclosed herein may prove advantageous to methods for "re-stenting" a lumen.

Figure 4A:
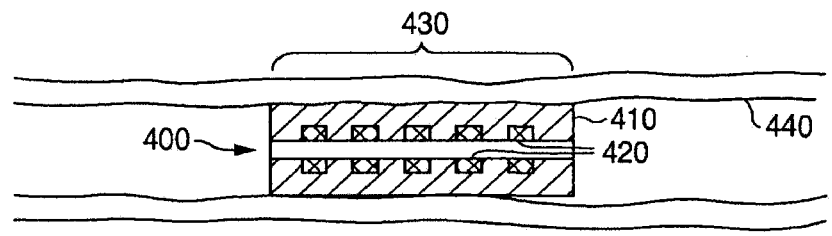
FIG. 4(a) depicts a cross section of a stent implanted in a body lumen, the stent having a scaffolding and depots.

In one embodiment, the stent includes depots in the stent scaffolding having depot material such as drug. According to one embodiment of the invention, one or more drugs or a drug-polymer mixture may be contained within at least one depot or cavity at the stent surface in at least a portion of the scaffolding. FIG. 4(a) depicts a cross section of a stent 400 having a scaffolding 410 and a plurality of depots filled with depot material 420. Stent 400 is implanted in a treatment site 430 of a lumen 440. Like the drug coating discussed above, the degradation rate of at least a portion of scaffolding 410 is faster than the degradation rate of all or substantially all depot material within the depots.

Figure 4B:
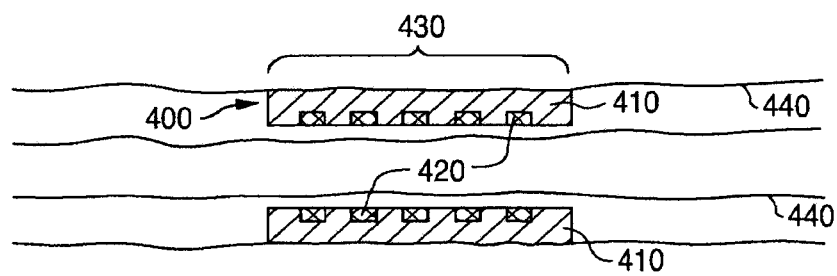
FIG. 4(b) depicts the stent of FIG. 4(a) after endothelialization of the stent in the body lumen.

In one embodiment, the degradation rate of all or substantially all of scaffolding 410 is faster than the degradation rate of all or substantially all of depot material 420 that is within the depots. Thus, the degradation time of all or substantially all scaffolding 410 is shorter than the degradation time of all or substantially all depot material 420. By providing a scaffolding 410 that has a faster degradation rate than its depot material 420, scaffolding 410 degrades away, while depot material 220 in the depots continues to deliver drug. In one embodiment, depot material 420 continues to deliver drug after scaffolding 410 has completely degraded. FIG. 4(b) depicts stent 400 after endothelialization of stent 400 in lumen wall 440. In one embodiment, all or substantially all of depot material 420 degrades faster than all or substantially all of scaffolding 410. In another embodiment, depot material 420 remains and continues to elute drugs even after scaffolding 410 no longer supports lumen wall 440.

Figure 4C:
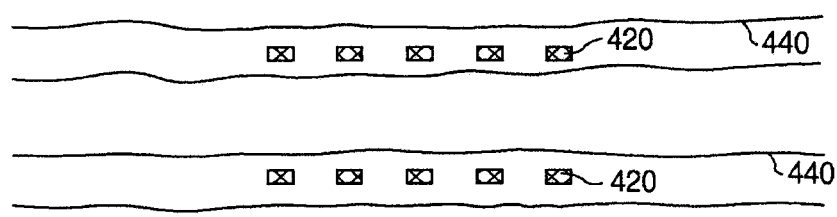
FIG. 4(c) depicts the stent of FIG. 4(a) after endothelialization of the stent and degradation of the scaffolding.

Turning now to FIG. 4(c), with continual reference to FIG. 4(b), depot material 420 remains lodged in lumen wall 440 after scaffolding 410 substantially degrades. Because depot material 420 can be made to deliver drug even after the disintegration of scaffolding 410, the invention enables stent 400 to release drug for an extended period of time throughout the life of stent 400 while scaffolding 410 degrades, and if desired, long after scaffolding 410 degrades. In one embodiment, stent 400 delivers drug for over 50% of the life of scaffolding 410. In another embodiment, stent 400 delivers drug for over 80% of the life of scaffolding 410. In yet another embodiment, stent 400 delivers drug for the entire life of scaffolding 410, or 100% of the life of scaffolding 410. Thus, after the entire scaffolding 410 has completely degraded, depot material 420 may be designed to continue to deliver drug, as depicted in FIG. 4(c).

In one embodiment, upon deployment of stent 400 in the treatment area, scaffolding 410 substantially or completely degrades from treatment area before depot material 420 substantially or completely degrades. In another embodiment, depot material 420 delivers a drug to the lumen 440 during degradation of scaffolding 410 and after substantial or complete degradation of scaffolding 410. In yet another embodiment, depot material 420 becomes endothelialized in a lumen wall 440 and delivers a drug after the scaffolding has substantially or completely degraded.

Figure 5:
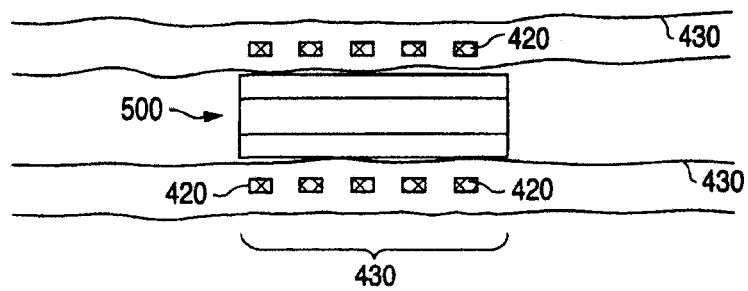
FIG. 5 depicts a second stent that is implanted at a treatment area of the first stent, where the scaffolding (not depicted) of the first stent has degraded.

Depicted in FIG. 5 is a second stent 500 that has been implanted in the same treatment area 430 as the first stent 400. In some embodiments, second stent 500 is implanted in the lumen at treatment area 430 after endothelialization of first stent. As depicted in FIG. 5, depot material 420 of first stent remains lodged in lumen 430. In some embodiments, second stent 500 is implanted in lumen 430 after a scaffolding (not depicted) of a first stent 500 is at least partially degraded, substantially degraded, or more narrowly, completely degraded in lumen 430. In some embodiments, second stent 500 is deployed in treatment area 410 when scaffolding (not depicted) of the first stent is greater than 50% degraded, greater than 75% degraded, and more narrowly, greater than 95% degraded as known of those skilled in the art.

In one embodiment, second stent 500 may be implanted in treatment area 430 after all or substantially all of scaffolding of first stent has degraded, such that only depot material 420 in the depots of first stent remains in the lumen. In certain embodiments, depot material of first stent 400 continues to deliver drug when second stent 500 is implanted.

As discussed above, a drug(s) may be included in depot material 420 of the first stent or the scaffolding (not depicted). Thus, when second stent 500 is implanted, the first stent may deliver drug from at least a portion of depot material 420 of first stent 400 while second stent 500 is implanted. For example, an anti-inflammatory agent may be included within depot material 420 of first stent 400, such that when scaffolding of second stent 500 is implanted, depot material 420 continues to deliver an anti-inflammatory agent to prevent inflammation. As mentioned above, the anti-inflammatory agent that is delivered from depot material 420 of first stent 400 may also effectively suppress inflammation of a lumen during all or a majority of the degradation of the scaffolding (not depicted) of first stent 400.

In a further embodiment, an anti-inflammatory drug and/or an anti-proliferative drug is included in the depots and/or the scaffolding of the stent and is designed to have certain release parameters for the drugs. Second stent 500 may have a biostable or biodegradable scaffolding made from a metal, polymer, or combination thereof. Second stent 500 may or may not include a coating, depots, or a drug.

In some embodiments, a coating is deposited over a scaffolding having depots. For example, the scaffolding may include a coating that may degrade at a slower rate than the scaffolding. The coating may be included in addition to the slow-degrading depot material. In some embodiments, the depot material, the coating material, and the scaffolding can be fabricated to have different degradation rates. For example, the coating material may have the slowest degradation rate, such that the depot material and scaffolding degrade prior to the coating. Thus, the coating material can be made to elute drugs during or after degradation of the depots or the scaffolding. The depot material could have the same degradation rate as the coating material. Alternatively, the depot material could have a slower degradation rate as the coating.

The depots may be designed in a variety of shapes and depths, depending on the desired delivery profile of the drug (s). For example, the depots may be formed having a cylindrical, a conical, or an inverted-conical shape. The depots may be formed into the stent by methods known to those of skill in the art. Depots may be formed on a body of the stent by exposing a surface of the stent to an energy discharge from a laser, such as an excimer laser. Alternative methods of forming depots include, but are not limited to physical or chemical etching techniques. Depots can be formed in virtually any stent structure and not merely the above-described structure.

Numerous embodiments of a stent with depots configured to hold a drug are possible. Depots may be placed at one or more arbitrary locations on a stent. The greater inflammation may arise from a larger concentration of degradation products closer to the center of the stent than the ends of the stent. Thus, the center of the lesion may require more anti-inflammatory agent than the ends of the lesion. Alternatively, the ends of the lesion may be more inflamed due to mechanical stresses causing irritation or injury to the ends of the lesion. Thus, a stent may include depots or more depots in regions of a stent adjacent portions of a lesion having more inflammation.

The coating or depot material may include a drug, a cell, a gene, a bioactive agent, or other therapeutic substances. In some embodiments, the drug coating or depot material may include a bioactive agent. A "bioactive agent" is a moiety that is mixed, blended, bonded or linked to a polymer coating or depot material, or to a polymer from which a stent scaffolding is made, and provides a therapeutic effect, a prophylactic effect, both a therapeutic and a prophylactic effect, or other biologically active effect upon release from the stent. The bioactive agents of the present invention may remain linked to a portion of the polymer or be released from the polymer. It should also be understood by those skilled in the art that multiple drugs can be included in a single depot, multiple depots, or the coating material. The material in the depot can be drug mixed or dispersed in a polymer matrix. The polymer matrix can degrade at a slower rate than the scaffolding. Depot material can be deposited in the depots according to methods known to those of skill in the art.

In one embodiment, the stent includes an anti-proliferative agent that includes, but is not limited to, Everolimus, Rapamycin, and/or derivatives thereof. Everolimus is available under the trade name Certican™, Novartis Pharma AG, Germany. The anti-proliferative agent may be included within the coating or depot material and/or in the scaffolding's polymer matrix. In one embodiment, the anti-proliferative agent is intermixed or dispersed within the coating or depot material and/or in the scaffolding's polymer matrix. In certain embodiments, the anti-proliferative agent is included in the depot material, within the coating, and/or within the scaffolding.

The stent may also include an anti-inflammatory agent, such as Clobetasol, which is available under the trade name Temovate™, Glaxosmithkline, UK. The anti-inflammatory agent may be included within the coating or depot material's polymer matrix and/or in the scaffolding's polymer matrix. In one embodiment, the anti-inflammatory agent is intermixed or dispersed within the polymer matrix of the coating or depot material and/or intermixed or dispersed within the scaffolding's polymer matrix. In certain embodiments, the anti-inflammatory agent is included within the depot material and/or the scaffolding.

The release of inflammation-inciting by-products into the body from a biodegradable device can occur continuously while the scaffolding is degrading within the body. An anti-inflammatory included within the scaffolding may allow for sustained release of the inflammatory agent throughout the degradation of the scaffolding. The drug-delivery stent disclosed herein may include a sustained release of an anti-inflammatory agent from the scaffolding. After the scaffolding absorbs, the coating or depot material in the lumen wall remains to deliver drug in the lumen.

As discussed above, underlying stent scaffolding may be made from a polymeric material that degrades more rapidly than the polymer used to form the coating or depot material. Any biodegradable polymer may be used to the form the scaffolding and the coating or depot material, as long as the polymer used to make all or substantially all the scaffolding degrades faster than the polymer used to make all or substantially all the coating or depot material. In some embodiments, the scaffolding can be formed of a copolymer that includes two functional groups or units. One of the units tends to increase the degradation rate compared to a homopolymer including the other unit.

In one embodiment, the stent scaffolding is formed of poly(D,L-lactide). In another embodiment, the stent scaffolding is formed of poly(D,L-lactide-co-glycolide), where 10% of the copolymer is D,L-lactide and 90% of the copolymer is glycolide. In another embodiment, the stent scaffolding is formed of poly(L-lactide-co-glycolide), where 10% of the copolymer is D,L-lactide and 90% of the copolymer is glycolide. In this embodiment, any polymer that degrades at a slower rate than poly(D,L-lactide-co-glycolide) may be used to form the coating/depot material. For example, poly(L-lactide) (PLLA) can be used to form a coating or depot material because PLLA is slower degrading than poly(D,L-lactide-co-glycolide). In another embodiment, the stent scaffolding is formed of poly(D,L-lactide-co-glycolide), where 5-45% of the copolymer is D,L-lactide and 55-95% of the copolymer is glycolide. In yet another embodiment, 1:1 mixture of Everolimus and poly(D,L-lactide) is used to form the coating or depot material, which completely degrades at about 12 months and has the ability to deliver drug for 3 months. Thus, the drug will be delivered even after the scaffolding has degraded, or has been absorbed into the body, or no longer supports the lumen. In certain embodiments, a scaffolding can be fabricated that degrades within 6 months, within 3 months, or more narrowly within 2 months.

Other material may also be used to fabricate the stent scaffolding, so long as all or substantially all of the scaffolding degrades at a faster rate than all or substantially all of the coating or depot material. In one embodiment, the coating or depot material includes Everolimus and poly(D,L-lactide) of a 1:1 ratio, and the scaffolding includes D,L-lactide and glycolide monomers in a 1:9 ratio with poly(D,L-lactide-co-glycolide).

As described above, it is also possible to have a sustained release of an anti-inflammatory agent from the coating or depot material. The anti-inflammatory agent may be included within the coating and/or depot material and is delivered from the coating and/or depots. The coating and/or depot material may be configured to sustain delivery of anti-inflammatory agent throughout the degradation of a stent scaffolding to counteract the inflammatory effect of the degradation of by-products of the scaffolding.

In one embodiment, an anti-inflammatory agent is included in both the coating material and the scaffolding. In another embodiment, an anti-inflammatory agent is included in both the depot material and the scaffolding. In another embodiment, an anti-inflammatory agent is included in the coating, depot material, and the scaffolding. Thus, an anti-inflammatory agent may be delivered from the coating, depots, and/or the scaffolding to suppress inflammation of a body lumen during all or a majority of the degradation of the scaffolding.

Any drugs having anti-inflammatory effects can be used in the present invention. The anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclprofen, cintazone, cliprofen, Clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

The anti-proliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, Everolimus, structural derivatives and functional analogues of rapamycin, structural derivatives and functional analogues of Everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof.

The relative amount of the anti-proliferative agent and/or anti-inflammatory agent in the stent can be determined by the lumen to be treated. For example, where Everolimus is used as the anti-proliferative agent and Clobetasol is used as the anti-inflammatory agent, the relative amount of Everolimus and Clobetasol can be varied for different types of lesions, that is, the relative amount of Everolimus can be higher for more proliferative lesions, and on the other hand, the relative amount of Clobetasol can be higher for more inflammatory lesions.

In some embodiments, other agents can be used in combination with the anti-proliferative agent and the anti-inflammatory agents. These bioactive agents can be any agent which is a therapeutic, prophylactic, or diagnostic agent. These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

Representative examples of polymers that may be used to fabricate the scaffolding, the coating material, and the depot material, or to provide a drug delivery particle with the anti-proliferative drug and/or anti-inflammatory drug include, but are not limited to poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially suited for use in fabricating the scaffolding, the coating material, and the depot material according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

In some embodiments, scaffolding material can also be fabricated from erodible metals. Metals may be biostable or bioerodible. Some metals are considered bioerodible since they tend to erode or corrode relatively rapidly when implanted or when exposed to bodily fluids. Biostable metals refer to metals that are not bioerodible. Biostable metals have negligible erosion or corrosion rates when implanted or when exposed to bodily fluids. Representative examples of biodegradable metals that may be used to fabricate a stent include, but are not limited to, magnesium, zinc, and iron.

A coating can be formed on a stent or depot material deposited in depots in a stent using spraying, dipping, or other methods known in the art. In such methods, the components of the coating or depot material are dissolved or suspended in a fluid to form a coating solution. For example, a polymer is dissolved in a suitable solvent and a drug is dissolved or suspended in the solvent. The coating solution is then applied to the stent. The solvent is then removed, leaving a coating or depot material within depots. "Solvent" is defined as a substance capable of dissolving or dispersing one or more other substances or capable of at least partially dissolving or dispersing the substance(s) to form a uniformly dispersed solution at the molecular- or ionic-size level. The solvent should be capable of dissolving at least 0.1 mg of the polymer in 1 ml of the solvent, and more narrowly 0.5 mg in 1 ml at ambient temperature and ambient pressure.

In some embodiments, a coating can include a primer layer and/or topcoat layer. The primer is beneath a drug/therapeutic substance layer and the topcoat layer above it. A topcoat layer can also be included over depots. Both the primer layer and the topcoat layer can be without any drugs/therapeutic substances. In some embodiments, some drug may incidentally migrate into the primer layer or region. The primer layer improves adhesion of the drug layer to the stent surface. The topcoat layer reduces the rate of release of the drug from the coating and/or depots and/or provides for bio-beneficial properties.

Although embodiments disclosed herein are focused on stents, the embodiments may be applied to any implantable medical device having a coating and/or depots on a substrate. The stent or drug-delivery system disclosed herein can be used to treat or prevent a disorder including but not limited to thrombosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, restenosis and progression of atherosclerosis in patient subsets including type I diabetics, type II diabetics, metabolic syndrome and syndrome X, vulnerable lesions including those with thin-capped fibroatheromatous lesions, systemic infections including gingivitis, hellobacteria, and cytomegalovirus, and combinations thereof.

A stent having the above-described coating or depot material is useful for a variety of medical procedures, including, by way of example, treatment of obstructions caused by tumors in bile ducts, esophagus, trachea/bronchi and other biological passageways. A stent having the above-described coating material is particularly useful for treating occluded regions of body lumens caused by abnormal or inappropriate migration and proliferation of smooth muscle cells, thrombosis, and restenosis. Stents may be placed in a wide array of body lumens, both arteries and veins. Representative examples of sites include the iliac, renal, and coronary arteries.

While particular embodiments of the present invention have been depicted and described, it will be obvious to those skilled in the art that changes and modifications can be made without departing from this invention in its broader aspects.

What is claimed is:

1. A method of treating a body lumen, the method comprising:
    providing a stent comprising a scaffolding having a plurality of depots and each filled with a depot material, wherein the scaffolding degrades at a faster rate than the depot material; and
    deploying the stent at a treatment area in a body lumen, wherein upon deployment, the stent becomes endothelialized within a wall of the lumen and after a degradation time of the scaffolding, the scaffolding completely absorbs away leaving the depot material lodged within a wall of the lumen at a plurality of locations of the depots, and
    wherein after a degradation time of the depot material, the depot material left lodged within the wall of the lumen completely absorbs away from within the wall of the lumen.

2. The method according to claim 1, wherein the stent includes an anti-proliferative agent, an anti-inflammatory agent, or a mixture thereof.

3. The method according to claim 1, wherein an anti-inflammatory agent is mixed or dispersed within the scaffolding.

4. The method according to claim 1, wherein an anti-inflammatory agent and an anti-proliferative agent is delivered from at least a portion of the depots.

5. The method according to claim 1, wherein an anti-inflammatory agent is delivered from the scaffolding and suppresses inflammation of the lumen during all or a majority of the absorption of the scaffolding.

6. The method according to claim 1, wherein the depot material delivers a drug to the lumen during absorption of the scaffolding and after substantial or complete absorption of the scaffolding.

7. The method according to claim 1, wherein the depot material lodged in the wall of the lumen delivers a drug after the scaffolding has substantially or completely absorbed.

8. The method according to claim 1, wherein the scaffolding comprises a bioabsorbable polymer and the depot material comprises a mixture of a drug and a bioabsorbable polymer.

* * * * *